United States Patent [19]
Nunokawa

[11] Patent Number: 6,156,516
[45] Date of Patent: Dec. 5, 2000

[54] METHOD FOR SCREENING SUBSTANCE INHIBITING ACTIVATION OF NF-κB

[75] Inventor: Yoichi Nunokawa, Toyonaka, Japan

[73] Assignee: Suntory Limited, Osaka, Japan

[21] Appl. No.: 09/272,706

[22] Filed: Mar. 19, 1999

[30] Foreign Application Priority Data

Mar. 20, 1998 [JP] Japan .................................. 10-090664

[51] Int. Cl.$^7$ .......................... C12Q 1/68; C07H 21/04; C12N 1/00; C12N 5/10; C12N 15/63
[52] U.S. Cl. .......................... 435/6; 435/243; 435/320.1; 435/325; 435/410; 536/24.1
[58] Field of Search ........................ 536/24.1; 435/320.1, 435/325, 410, 243

[56] References Cited

PUBLICATIONS

Altered Immune Responses in Mice Lacking Inducible Nitric Oxide Synthase, Xiao–quin Wei et al., Letter to Nature, vol. 375, Jun. 1, 1995, pp. 408–411.

Altered Responses to Bacterial Infection and Endotoxic Shock in Mice Lacking Inducible Nitric Oxide Synthase, MacMicking et al., Cell, vol. 81, May 19, 1995, pp. 641–650.

Promoter of the Mouse Gene Encoding Calcium–Independent Nitric Oxide Synthase Confers Inducibility by Interferon γ and Bacterial Lipopolysaccharide, Qiao–wen Xie et al., J. Exp. Med. vol. 177, Jun. 1993, pp. 1779–1784.

Mechanisms of Suppression of Macrophage Nitric Release by Transforming Growth Factor β, Vodovotz, et al., J. Exp. Med. vol. 178, Aug. 1993, pp. 605–613.

Role of Interferon Regulatory Factor 1 in Induction of Nitric Oxide Synthase, Martin, etal., J. Exp. Med. vol. 180, Sep. 1994, pp. 977–984.

Role of Transcription Factor NF–kB/REL in Induction of Nitric Oxide Synthase, Blackwell et al, Journal of Biol. Chem., vol. 269, No. 7, Feb. 18, 1994, pp. 4705–4708.

Macrophage Nitric Oxide Synthase Gene: Two Upstream Regions Mediate Induction by Interferon γ and Lipopolysaccharide, Lowenstein et al., Proc. Natl. Acad. Sci., vol. 90, Oct. 1993, pp. 9730–9734.

Requirement for Transcription Factor IRF–1 in no Synthase Induction in Macrophages, Kamijo, et al., Science, vol. 263, Mar. 18, 1994, pp. 1612–1615.

Molecular Cloning and Expression of Inducible Nitric Oxide Synthase from Human Hepatocytes, Geller et al., Proc. Natl. Acad. Sci, vol. 90, Apr. 1993, pp. 3491–3495.

Purification and cDNA Sequence of an inducible Nitric Oxide Synthase from a Human Tumor Cell Line, Sherman et al., Biochemistry, 32, 1993, pp. 11600–11605.

Cloning, Characterization, and Expression of a cDNA Encoding an Inducible Nitric Oxide Synthase from the Human Chondrocyte, Charles et al., Proc. Natl. Acad. Sci., vol. 90, Dec. 1993, pp. 11419–11423.

Molecular Cloning, Structure, and Chromosomal Localization of the Human Inducible Nitric Oxide Synthase Gene, Chartrain et al., Journ. of Biological Chem., vol. 269, No. 9, Mar. 4, 1994, pp. 6765–6772.

Cloning of Inducible Nitric Oxide Synthase in Rat Vascular Smooth Muscle Cells, Nunokawa, et al., Biochem. and Biophys. Res. Commun. vol. 191, No. 1, Feb. 26, 1993, pp. 89–94.

Promoter Analysis of Human Inducible Nitric Oxide Synthase Gene Associated with Cardiovascular Homestasis, Nunokawa, et al., Biochem. and Biophys. Res. Commun. vol. 200, No. 2, Apr. 29, 1994, pp. 802–807.

Transcriptional Regulation of Human Inducible Nitric Oxide Synthase (NOS2) Gene by Cytokines: Initial Analysis of the Human NOS2 Promoter, Procl. Natl. Acad. Sci., vol. 93, Feb. 1996, pp. 1054–1059.

Glucocorticoids Inhibit the Induction of Nitric Oxide Synthase II by Down–Regulating Cytokine–Induced Acvitity of Transcription Factor Nuclear Factor–kB, Kleinert et al., Mol. Pharc., 49:15–21 (1996), pp. 15–21.

Human Inducible Nitric Oxide Synthase Gene is Transcriptionally Regulated by Nuclear Factor–kB Dependent Mechanism, Nunokawa et al., Bioc. and Biophs. Res. Comm., 223, (1996) No. 0897, pp. 347–352.

The Role of Nuclear Factor–kB in cytokine Gene Regulation, Blackwell et al., Am. J. Respir. Cell. Mol. Biol., vol. 17, 1997, pp. 3–9.

*Primary Examiner*—Terry McKelvey
*Attorney, Agent, or Firm*—Burns, Doane, Swecker & Mathis, L.L.P.

[57] ABSTRACT

An expression regulatory sequence comprising a NF-κB recognition sequence, at least part of the 3'-untranslated region (3'-UTR) and at least part of the 3'-flanking region of human induced nitrogenmonoxide synthase (hiNOS) gene; and a method for screening a substance repressing the activation of NF-κB, comprising treating cells having the expression regulatory sequence and capable of detecting the activation of NF-κB with a subject substance, and observing a change in the expression amount of reporter genes.

17 Claims, 15 Drawing Sheets

Fig. 1

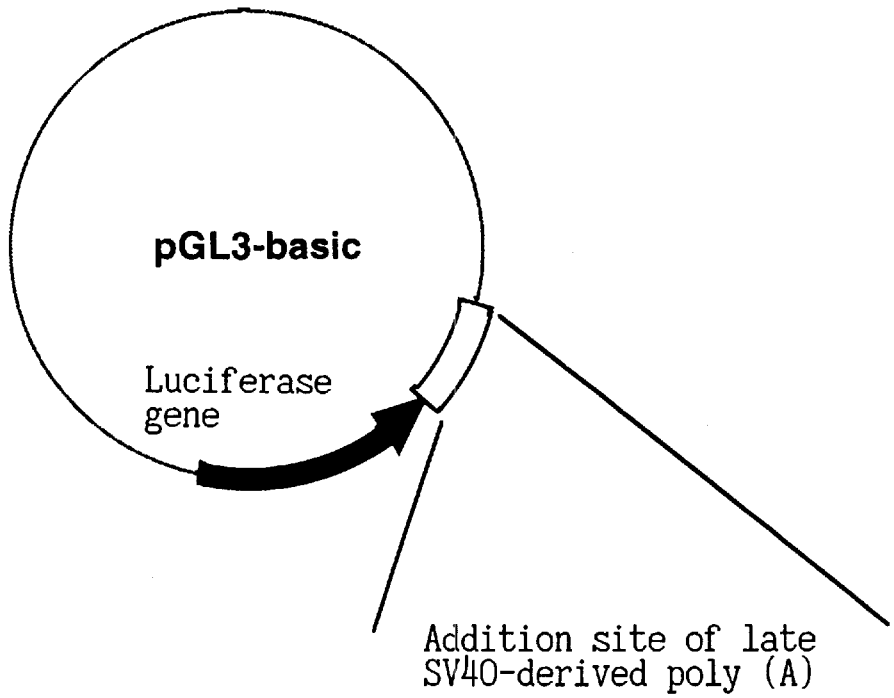

Addition site of late SV40-derived poly (A)

5'- CTAGAGTCGGGGCGGCCGGCCGCTTCGAGCAGACATGATAAGATACATTG
ATGAGTTTGGACAAACCACAACTAGAATGCAGTGAAAAAAATGCTTTATT
TGTGAAATTTGTGATGCTATTGCTTTATTTGTAACCATTATAAGCTGC<u>AA</u>
<u>TAAA</u>CAAGTTAACAAC<u>A</u>ACAATTGCATTC<u>ATTTTATGTTT</u>CAGGTTCAGG
        ↑
     poly (A) Addition
GGGAGGTGTGGGAGGTTTTTTAAAGCAAGTAAAACCTCTACAAATGTGGT
AAAATCGATAAGGATCCGTCGACCGATGCCCTTGAGAGCCTTCAAC -3'

Fig. 2

```
3619                                                     AGCCAGAAGCGCTATCACGAAGATATCT
                                                                    SA101
3647 TCGGTGCTGTATTCCTTACGAGGCCAAGAAGGACAGGGTGGCGGTGCAGCCCAGCAGCCTGGAGATGTCAGGCCTC
                                                                    SA102
3724 TGAGGGCCTACAGAGAGGGTTAAAGCTGCCGGCACAGAACTTAAGGATGGAGCCAGCTCTGCATTATCTGAGGTCAC
            SA103
3801 AGGGCCTGGGGGAGATGGAGGAAAGTGATATCCCCCAGCCTCAAGTCTTATTCCTCAACGTTGCTCCCCATCAAGCC
3878 CTTTACTTGACCTCCTAACAAGTAGCACCCTGGATTGATCGAGCCTCTCAAACTGCTGGGCCTCCCGTCCC
3955 TTGGAGACAAATCTTAAATGCCAGGCCTGGGCCAGTGGGTGAAAGATGAACTGCTGCTGAGTGCACCACTTCAAG
4032 TGACCACCAGGAGGTGCTATCGCCACCACTGGTATTTAACTGCCTTGTGTACAGTTATTTATGCCTCTGTATTTAAA
4109 AAACTAACACCCAGTCTGTCCCCATGGCCACTTGGGTCTTCCCGTATGATTCCTTGATGGAGATATTTACATGAA
                 KI102
4186 TTGCATTTTACTTTAATCAC ↑ AAAAAAAA..........
          KI101/KI104
```

Fig. 3

Wild type hiNOS cDNA sequence    5'-ATGGCCTGTGTCCCT̲TGGAAATTTCTGTT-3'

Mutant sequence    5'-ATGGCCTGTGTCCCCA̲TGGAAATTTCTGTT-3'

Fig.4

| SU802 | 5'-CTTCTCAGCCACCTTGGTGAGG-3' |
| MI103 | 5'-TTCTGTGCAGTCCCAGTGAGG-3' |
| SA101 | 5'-AGCCAGAAGCGCTATCACG-3' |
| KI101 | 5'-TGTGATTAAAGTAAAATGCAATTCATG-3' |
| SA102 | 5'-GCCTGGAGATGTCAGCGCTCTG-3' |
| KI102 | 5'-GGGGAACAGACTGGGTGTTAG-3' |
| KI103 | 5'-CATTTAGGTGACACTATAG-3' |
| SA103 | 5'-GGCGCTAGCCTACAGGAGGGGTTAAAGCT-3' |
| KI105 | 5'-GCGCGGATCCGGCCCACTCTCCTAAG-3' |

Fig. 5

```
3724 TGAGGGCCTACAGGAGGGGTTAAAGCTGCCGGCACAGAACTGCCGGAGCCAGCTCTGCATTATCTGAGGTCAC
3801 AGGGCCTGGGGAGATGGAGGAAAGTGATATCCCCCAGCCTCAAGTCTTATTCCTCAACGTTGCTCCCATCAAGCC
3878 CTTTACTTGACCTCCTAACAAGTAGCACCCTGATTGATCGGAGCCTGAGTGAGCCTCAAACTGGGGCCTCCTGTCCC
3955 TTGGAGACAAAATCTTAAATGCCAGCCTGGGCGAGTGGGTGAAAGATGGAACTTGCTGCTGAGTGCACCACTTCAAG
4032 TGACCACCAGGAGGTCTATCGCCACCACTGTGTATTTAACTGCCTTGTGTACAGTTATTTATGCCTCTGTATTTAAA
4109 AAACTAACACCCAGTCTGTCCCCATGGCCACTTGGGTCTTCCCCTGTATGATTCCTGATGGAGATATTTACATGAA
4186 TTGCATTTTACTTTAATCAG ACTGTATGCTGTGTGTGTTTTGTAGGGAAAGCTCTTCTCAGAGTGGGAGCTGG
TGGGTGTCACAGCCTGGACAGATCCCGACAGAGGACACCCCAGCCAGTGCCTCCTGAAATGGCTGCCAG
GTGTGCCAGCAGCAGGATGGAGCTTCGTGGTCCAAAGACCTTGTGAGGGCCTGGCAGGGGCCTGCCTCCAC
ACAAAGTATCTGAAACGGGGTCTGGTGAGGGTGGATTGTCGCATAAGGCCAGTGTTTCGAGGAAGGCCTTGAGCTT
CTTCTTGACACTGTCTTAGAAGGCGTTTGCTCTGGGCAGTGTGTGCCGAGACTGTGTGCCTTGCCTTGCCAGTA
CGGATGTGGTCCCTGGGAGCAGCAGCAGCTGTGGCCACAACATCCTGCCGAGGACTGGGACCC
TCTTGGGTTTGAAGCTCAAGGAGAATCCTTCTTAGGAGAGTGGGCCCGTTCCTTCCTCGGTTGTCAGAACCCAAAA
                                                        ←KI105
AGGAGCTCAGCGGCGGCCACTGGGGNNNNNNNNNNNNNN
```

Fig.6
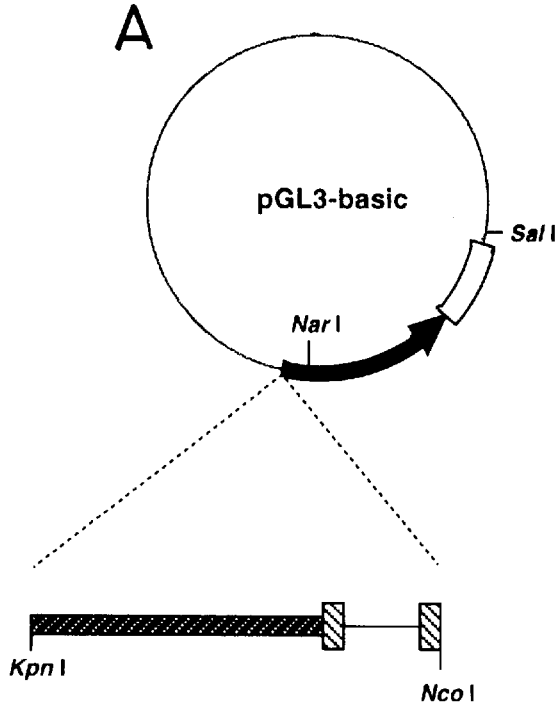
pGLNOS5+SV3
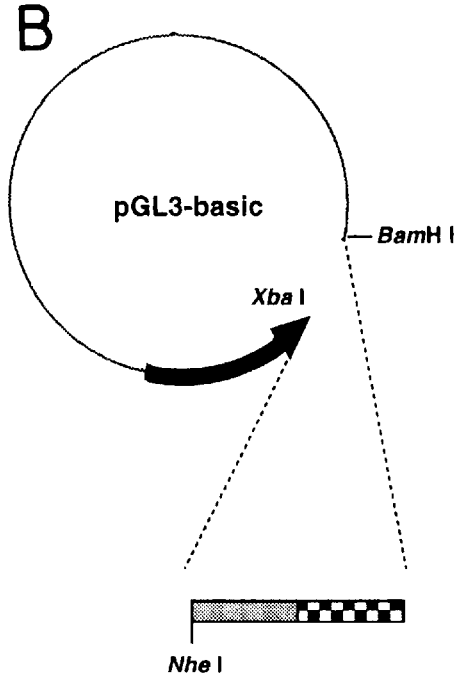
pGLNOS3A
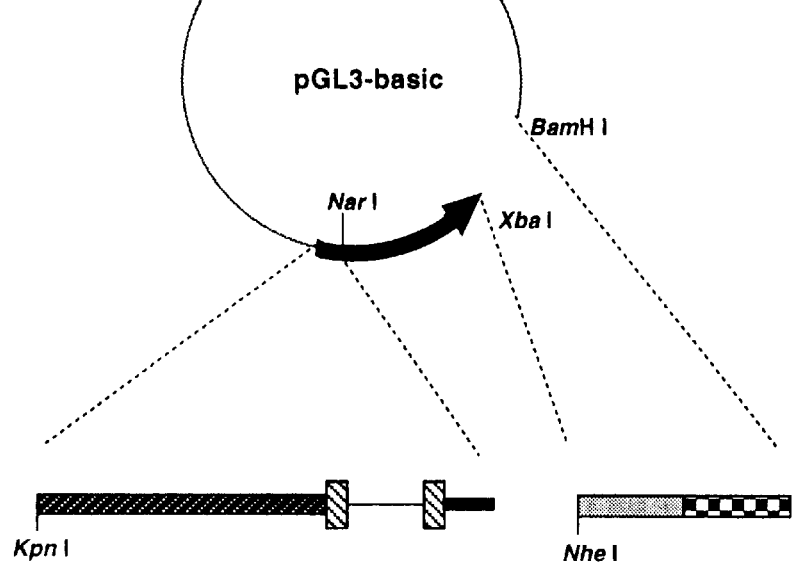
pGLNOS53A

Fig. 15
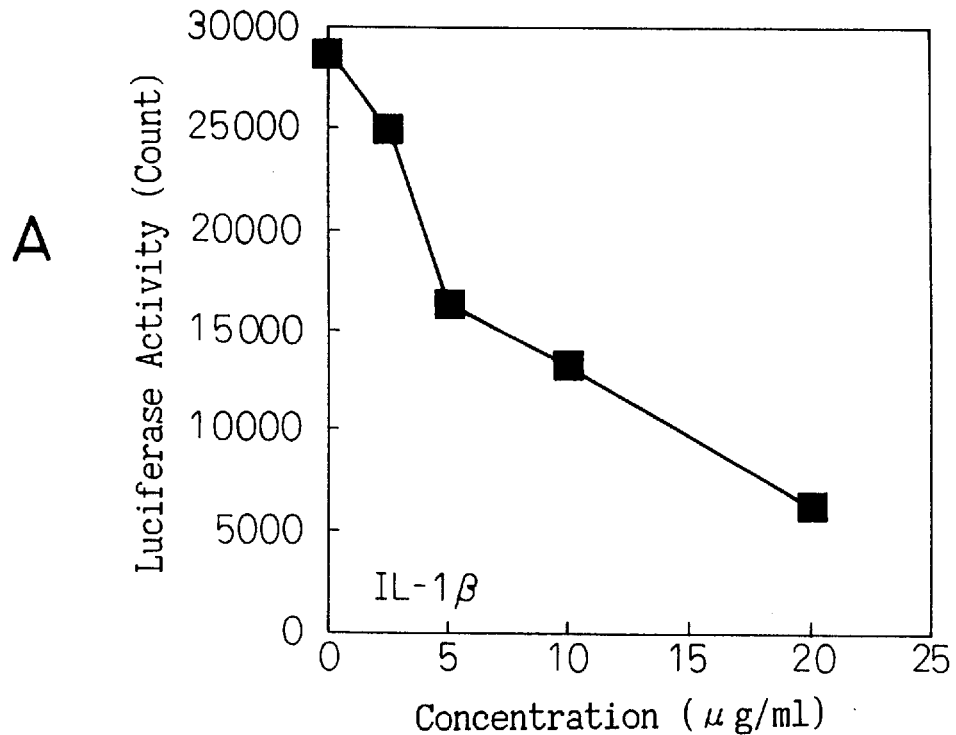
A
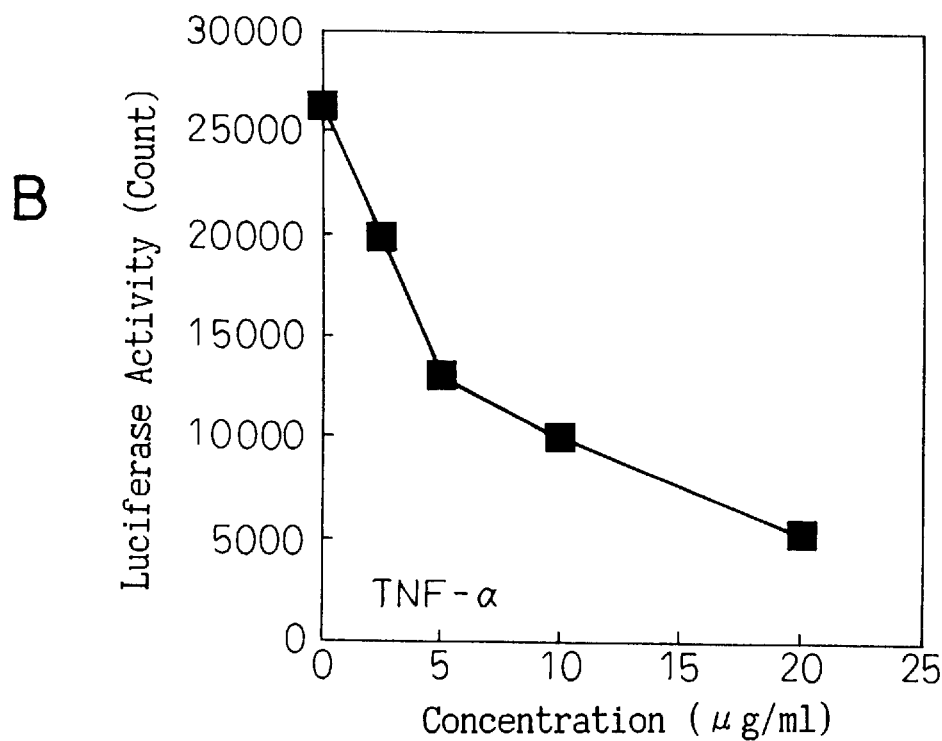
B

Fig. 16
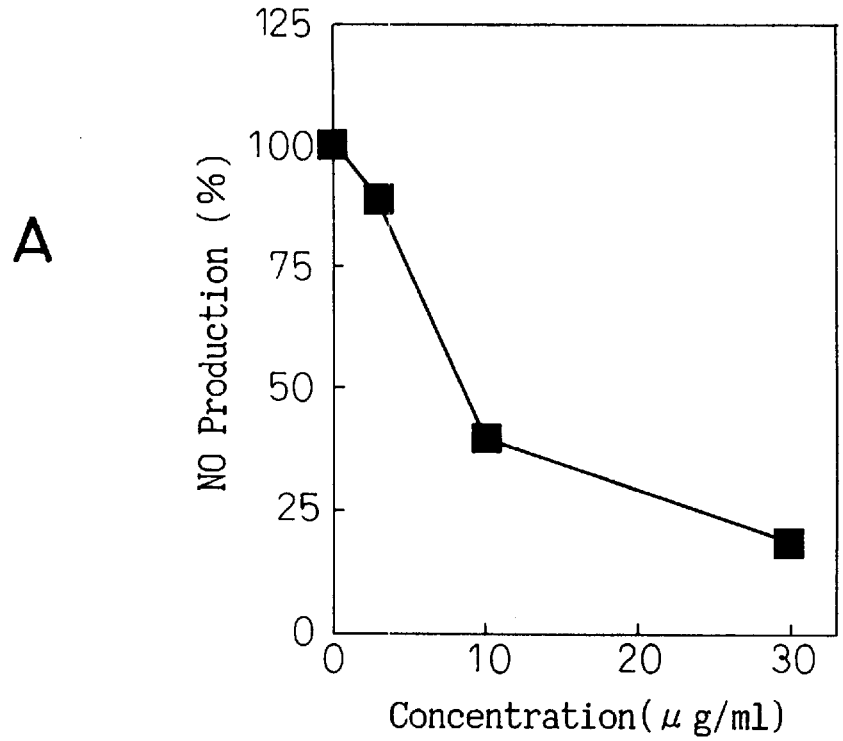
A
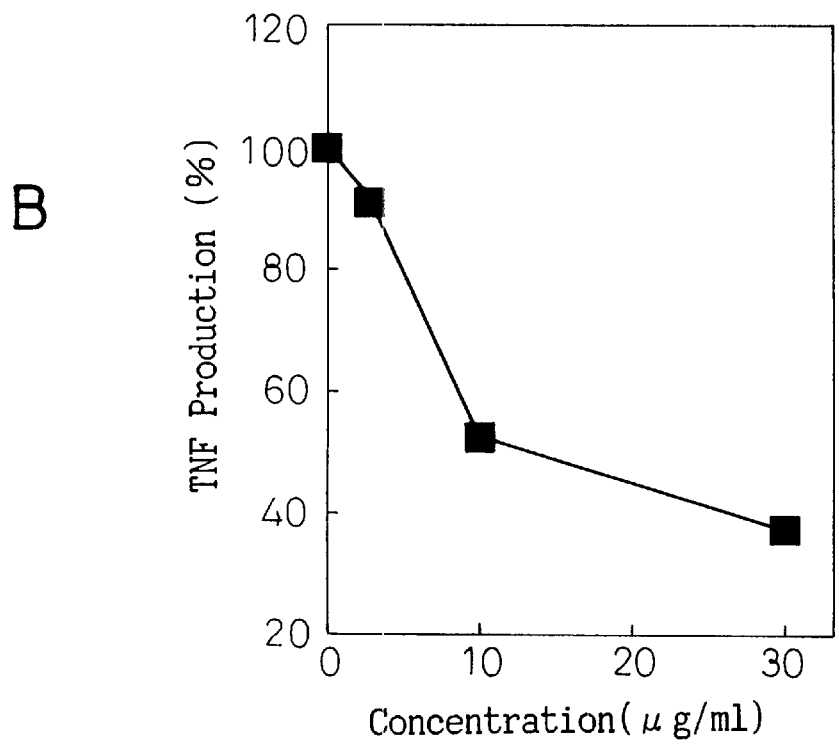
B

METHOD FOR SCREENING SUBSTANCE INHIBITING ACTIVATION OF NF-κB

BACKGROUND OF INVENTION

1. Field of Invention

The present invention provides a method for screening and evaluating a synthetic compound or naturally occurring compound which inhibits an activation of NF-κB, simply and highly sensitively by utilizing a gene having a sequence which regulates the expression of human inducible nitric oxide synthase (hiNOS) gene.

2. Related Art

It has been clarified that an inflammatory disease is caused by the production of many types of mediators. Development of the remedy of the inflammatory disease is made difficult because the cause of the disease cannot be attributed to one mediator. One of the factors regulating the production of the mediators is activation of NF-κB.

NF-κB is a protein which regulates a gene expression, and is one of the so-called transcription factors. When a normal cell is stimulated with an inflammatory cytokine such as interleukin (IL)-1, tumor necrosis factor (TNF)-α, a lipopolysaccharide, UV-rays, or the like, NF-κB is activated, moved into the nucleus from the cytoplasm, and binds to a specific nucleotide sequence on a genomic DNA, and participates in the expression of various genes (Blackwell, T. S. and Christman, J. W. (1997) Am. J. Respir. Cell. Mol. Biol., 17, 3–9).

Genes which are considered to be subjected to expression regulation by NF-κB are often those participating in immunity inflammation reactions such as inducible nitric oxide synthase (iNOS), inflammatory cytokines such as TNF-α, IL-1, IL-6 and IL-8, and cell adhesion molecules such as ICAM-1, VCAM-1 and ELAM-1 (Collins, T., Read, M. A., Neish, A. S., Whiteley, M. Z., Thanos, D. and Maniatis, T. (1955) Faseb. J., 9, 899–909). Moreover, when an inflamatory cytokine binds to its receptor, the cytokine is known to transduce a signal which activates NF-κB through various routes, which is considered to aggravate the inflammation. As explained above, the activation of NF-κB is understood to be a cause and an exacerbation factor of a variety of diseases (Baeuerle, P. A. and Baichwal, V. R. (1997) Adv. Immunol., 65, 111–137).

Furthermore, it has been reported in recent years that HIV, HTLV-1, CMV, adenovirus, or the like activates NF-κB in the host cells (Dezube, B. J., Pardee, A. B., Beckett, L. A., Ahlers, C. M., Ecto, L., Allen-Ryan, J., Anisowicz, A., Sager, R. and Crumpacker, C. S. (1992) J. Acquir. Immune Defic. Syndr., 5, 1099–1104, Nabel, G. and Baltimore, D. (1987) Nature, 326, 711–713, Fazley, F., Dezube, B. J., Allen-Ryan, J., Pardee, A. B. and Ruprecht, R. M. (1991) Blood, 77, 1653–1656, Munoz, E. and Israel, A. (1995) Immunobiology, 193, 128–136). Activation of NF-κB increases the transcription, proliferation and infectivity of the virus.

Furthermore, activation of NF-κB has been confirmed in various chronic inflammatory diseases (Marok R., Winyard P G, Coumbe A, Kus M L, Gaffney K, Blades S, Mapp P I, Morris C J, Blake D R, Kaltschmidt, Baeuerle P A (1996) Arthritis Rheum. 39, 583–591).

Activation of NF-κB influences the expression of genes related to a variety of inflammatory diseases, and, as already explained, iNOS is an example wherein the gene expression is influenced thereby. The iNOS is an enzyme whose substrate is L-arginine and which biosynthesizes nitric oxide (NO). For hiNOS, the complete structure of the structural gene including an about 0.4-kb sequence in the 5'-flanking region has been elucidated (Chartrain, N. A., Geller, D. A., Koty, P. P., Sitrin, N. F., Nussler, A. K., Hoffman, E. P., Billiar, T. R., Hutchinson, N. I., and Mudgett, J. S. (1994) J. Biol. Chem., 269, 6765–6772). Excessive NO produced due to the induction of the iNos is thought to wound normal cells to cause various symptoms.

It has been reported that iNOS is induced in any species by inflammation conditions, and it has been shown that the inhibition of the activity or the expression of the enzyme is effective in abatement of the symptom (Cattell, V. and Janse, A. (1995) Histochem. J., 27, 777–784, Nussler, A. K. and Billiar, T. R. (1993) J. Leukoc. Biol., 54, 171–178). Moreover, it has been shown in an experiment of the gene knockout mice of the mouse iNOS(miNOS) that the disruption of the gene leads to resistance to inflammation caused by sepsis or carrageenan. Accordingly, it has become evident that the inhibition of iNOS causes these symptoms (Wei, X. Q., Charles, I. G., Smith, A., Ure, J., Feng, G. J., Huang, F. P., Xu, D., Muller, W., Moncada, S. and Liew, F. Y. (1995) Nature, 375, 408–411).

Accordingly, if activated NF-κB can be inhibited, it is considered that the expression of not only iNOS but also other genes and viruses that encode inflammatory cytokines and adhesion molecules can be entirely repressed.

Under such situations, a low molecular weight compound is desired which can extensively inhibits the production and expression of protein relating to the cause of inflammation. Such a substance is particularly promising for remedies and prevention against diseases directly or indirectly caused by the activation of NF-κB, for example, for remedies and preventives against various autoimmune diseases, immunosuppressants, and remedies and preventives against virus infection.

However, since there is no satisfactory evaluation method which can be used for screening substances (specifically, candidate substances for pharmaceuticals) inhibiting the activity of NF-κB by evaluating the activation of NF-κB, a simpler and more highly sensitive evaluation method has been desired.

SUMMARY OF INVENTION

An object of the present invention is to provide a method capable of screening simply and highly sensitively a synthetic compound or naturally occurring compound which can inhibits an activation of NF-κB.

Accordingly, the present invention provides an expression regulatory sequence comprising an NF-κB recognition sequence, and at least part of a 3'-untranslated region (3'-UTR) and at least part of a 3'-flanking region of a human inducible nitrogen monoxide synthase (hiNOS) gene.

The present invention further provides an expression vector comprising the above-mentioned expression regulatory sequence.

The present invention further provides an expression vector comprising (1) the 5'-flanking region containing the promoter region of a hiNOS gene, (2) a reporter gene and (3) an expression regulatory sequence according to claim 1 or 2, in the order mentioned above from the 5'-side.

The present invention further provides a cell transformed with said expression vector.

The present invention further provides a method for screening a substance repressing an activation of NF-κB, comprising treating a cell having an expression regulatory sequence according to claim 1 or 2 and capable of detecting an activation of NF-κB with a test substance, and observing a change in the expression amount of the reporter gene.

The present invention also provide a kit for screening a substance inhibiting the activation of NF-κB, comprising said cells.

The present invention further provides compounds obtained by said screening method.

BRIEF DESCRIPTION OF THE DRAWINGS

FIG. 1 is a view showing the structure of a pGL3 basic plasmid and the nucleotide sequence (SEQ ID NO: 1) at the addition site of SV40-derived poly(A), "Poly(A) signal" and "GT cluster" participating in the poly(A) addition are underlined.

FIG. 2 shows the nucleotide sequence (SEQ ID NO: 2) of hiNOS cDNA exon 26. The numbers of the left ends show numbers of nucleotides when the nucleotide at the start of the translated region is defined as 1. The ATTTA sequence is underlined, and the anticipated poly(A)-addition site is shown with the mark ↑. The bold faces show the translation stop sequence in the hiNOS translation region. Moreover, the nucleotide sequences on which the primers used in the present invention are based are described.

FIG. 3 shows the substitution of nucleotides (SEQ ID NO: 11) for introducing a restriction enzyme Nco I site. CA is substituted for the nucleotide T shown by a bold face to construct a mutant plasmid.

FIG. 4 shows the sequences of PCR primers used in the present invention (SEQ ID Nos: 3–10 and 12). The recognition sites of the restriction enzymes are shown with underlines.

FIG. 5 shows the sequences of the 3'-UTR and 3'-flanking region of a hiNOS gene (SEQ ID NO: 13). The Nos. shown at the left ends are those when the nucleotide at the start of the translation region is defined as 1. The frame shows the 3'-UTR of exon 26. The recognition sequence (YGTGTTYY) for addition of poly(A) in the 3'-flanking region is indicated by an underline. The bold faces show the translation stop sequence in the hiNOS translation region. Moreover, the nucleotide sequence on which the primer used in the present invention is based is clearly described.

FIGS. 6A–6C show the construction of plasmids according to the present invention. A shows the plasmid pGLNOS+ SV3. B shows the plasmid pGLNOS3A. C shows the plasmid pGLNOS53A.

Figure 7:
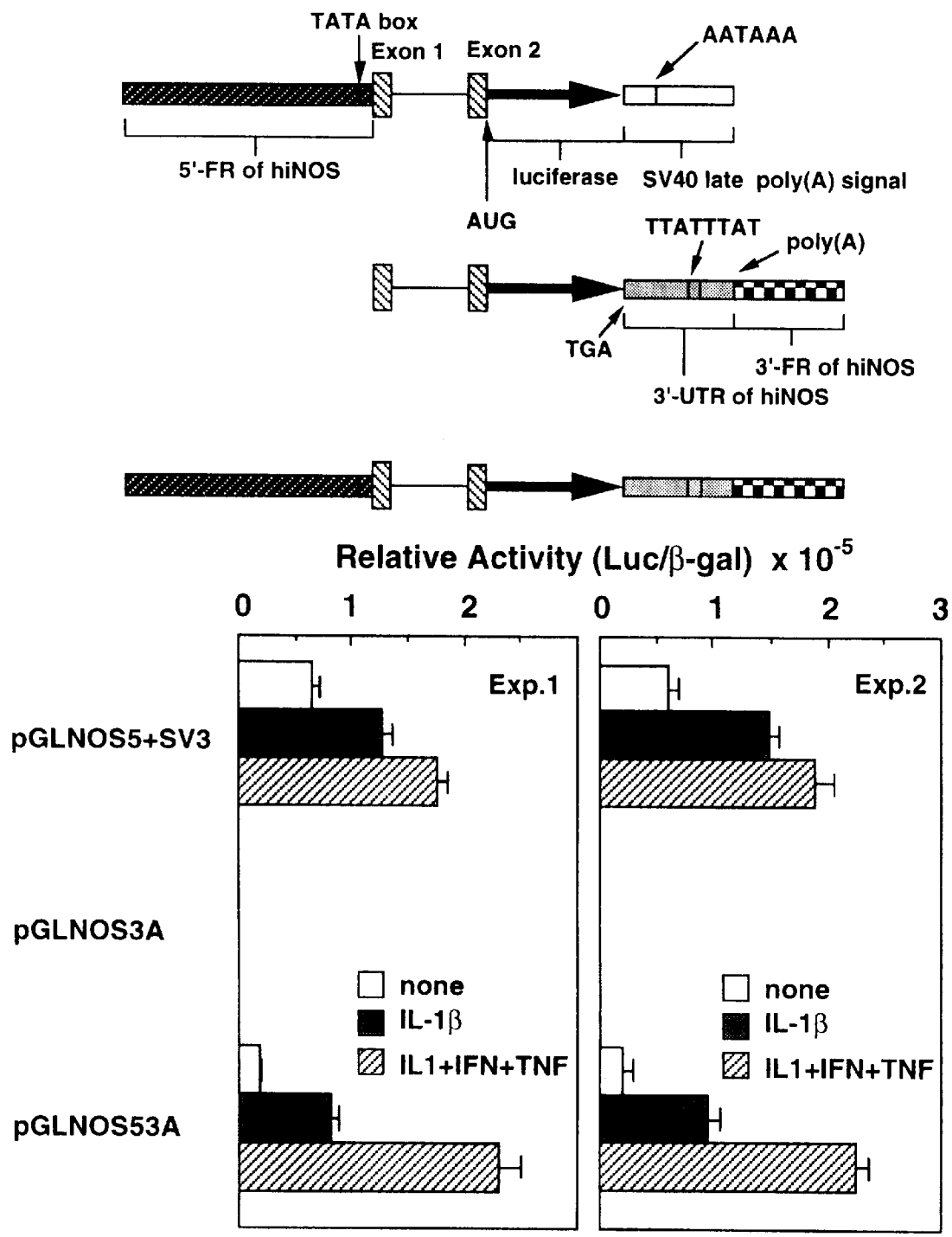
FIG. 7 shows the influence of cytokine stimulation on the 5'- and 3'-regions of a hiNOS gene in transient assay.

L indicates a complex of a labeled probe including a NF-κB recognition sequence and a nuclear extraction substance. F shows the experimental results when a non-labeled probe is added in an amount 100 times that of the labeled probe under the same conditions as in L.

FIGS. 15A–15B show the influence of compound I when A549/NF-κBLuc is stimulated with IL-1 or TNF-α. The compound I is added, and A549/NF-κBLuc is stimulated with IL-1 or TNF-α for 4 hours 1 hour after the addition. The results of measuring the activity of a reporter gene after stimulation are shown.

FIGS. 16A–16B are graphs showing the influence of the compound I on the production of NO and TNF-α after LPS stimulation using mouse macrophage-derived RAW264.7.

The compound I was added to a culture medium 1 hour before LPS stimulation, and the results of measuring the NO level in the culture medium 24 hours after the stimulation (A) and the TNF level therein 4 hours after the stimulation (B) are shown.

Figure 17:
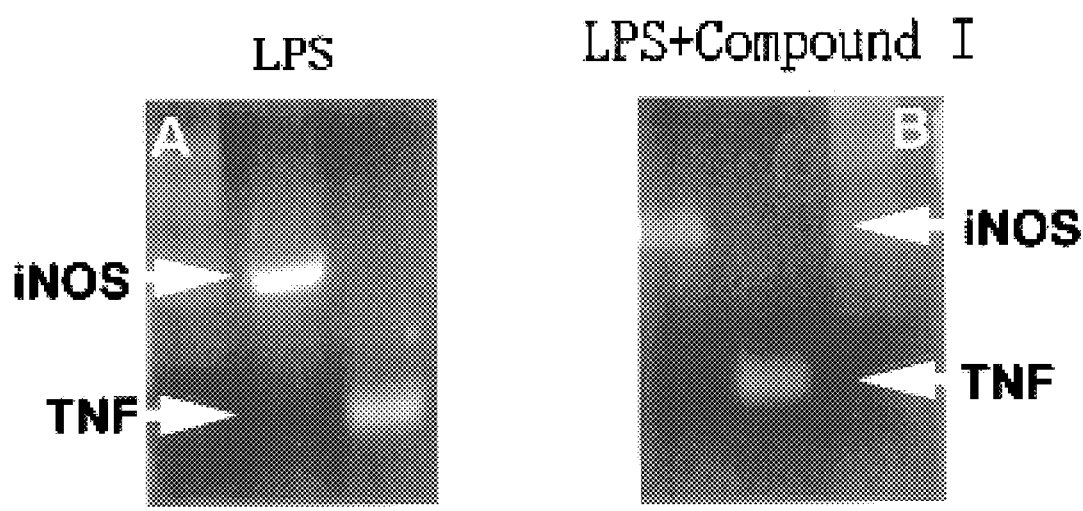

FIG. 17 shows changes in the amounts of mRNA of iNOS and TNF-α in a RAW264.7. cell.

A shows the results of measuring the iNOS mRNA level and TNF-α mRNA level within the cell 6 hours after LPS stimulation.

B shows the results of measuring the iNOS mRNA level and TNF-α mRNA level within the cell 6 hours after LPS stimulation. The compound I (20 μg/ml) had been added to the culture medium 1 hour before the LPS stimulation.

DETAILED DESCRIPTION

Reporter genes have been utilized for monitoring the expression of a certain gene simply and highly sensitively (Yokota, T. and Arai, K. (1993) Biomanual Series 4, Yodosha, K. K.). The reporter genes are used in place of directly detecting the expression of the test gene; chloramphenicol acetyltransferase (CAT), β-galactosidase (β-Gal), luciferase, and the like have been widely used as reporter genes at present. A plasmid is prepared in which a gene containing a recognition sequence for the transcription factor to be tested is inserted into the upstream or downstream of the translating region of the reporter gene; the activity of the transcription factor can be detected highly sensitively.

Many of the reporter genes which have commonly been used are constructed by incorporating an SV40-derived poly(A) region, for the purpose of expressing matured mRNA. A pGL3 basic plasmid (Promega, U.S.A.) used by the present inventors as well as plasmids having been employed in reports by other groups is also subjected to the construction (FIG. 1, SEQ ID NO: 1). Therefore, when the induction of the test gene does not entirely depend on the activation of transcription but also is caused by instability of the produced mRNA, it is thus necessary to incorporate the region involved in the instability of the produced mRNA into the expression vector containing the reporter gene.

In order to solve the problems associated with the present invention, the present inventors have paid attention to the possibility that the expression of a hiNOS gene having an NF-κB recognition sequence is regulated by the outside of the 5'-flanking region.

That is, the NF-κB recognition sequence is present in the hiNOS gene, and the expression of the hiNOS gene is thought to be regulated by NF-κB. However, the mechanism of regulating the expression of the gene currently has not been elucidated sufficiently. When a plasmid which contains a reporter gene drived by about 3.2 kb of the 5'-flanking region of the hiNOS gene is introduced into a call and analysis is carried out, the 5'-flanking region, even though in which the NF-κB recognition sequence is contained cannot explain the mechanism of the hiNOS induction (Nunokawa, Y., Oikawa, S., and Tanaka, S. (1996) Biochem. Biophys. Res. Commun., 223, 347–352). That is, the activation of NF-κB, concerned with the hiNOS expression, is controlled by not only the 5'-flanking region of the gene but also any other region.

On the other hand, when the sequence of the 3'-untranslation region (3'-UTR) in exon 26 (SEQ ID NO: 2; FIG. 2) of a hiNOS gene was examined, a sequence (AUUUA sequence) having been reported to play a role in destabilizing the mRNA was recognized in 4 portions (underlined portions in FIG. 2) in the region. Therefore, it was considered that there might be the possibility that induction of the hiNOS expression was controlled by a factor, which destabilizes the transcription products of the gene. Accordingly, it was thought that use of the 3'-UTR and 3'-flanking region of the gene could imitate the strong expression of the hiNOS gene, and detect the activation of NF-κB highly sensitively.

Accordingly, when about a 1-kb region containing the 3'-UTR and the 3'-flanking region of the gene was further inserted into the downstream of the reporter gene drived the promoter of the hiNOS gene in the above expression vector, the inserted region was found to participate in strong expression in corporation with the promoter region containing the NF-κB recognition region. That is, the expression of the reporter gene under noninducing conditions, which has been a problem in the conventional technologies, has disappeared, and the present inventors have established an evaluation system in which the NF-κB activity can be observed only by making cytokine act.

That is, evaluation of the activation of NF-κB which has been conventionally impossible up to now has become possible by utilizing the 3'-region of the hiNOS gene as explained in the present invention. Consequently, the present invention has achieved a method for screening a candidate compound (namely, a compound inhibiting the activation of NF-κB) for producing medicaments for the medical treatment of diseases caused by the activation of NF-κB.

The principal object of the present invention is to establish an evaluation system associated with the activation of NF-κB participating in the regulation of gene expression, and provide a method for simply and highly sensitively screening a synthetic compound or naturally occurring compound which can inhibits the activation of NF-κB. Specifically, the present invention includes the following aspects of invention.

(1) An expression regulatory sequence comprising a NF-κB recognition sequence, and at least part of the 3'-UTR and at least part of the 3'-flanking region of a hiNOS gene, or the expression regulatory sequence in which the 3'-flanking region comprises a nucleotide sequence of SEQ ID NO: 15.

(2) An expression vector further comprising an expression vector containing the expression regulatory sequence mentioned above, and a reporter gene.

(3) An expression vector comprising (a) the 5'-flanking region containing the promoter region of a hiNOS gene, (b) a reporter gene and (c) the expression regulatory sequence in the order as mentioned above from the 5'-side.

(4) A cell transformed with any one of the above expression vectors.

(5) A method for screening a substance inhibiting the activation of NF-κB, comprising treating cells having the above expression regulatory sequence with a test substance, and observing a change in the expression amount of the reporter gene.

(6) The above screening method, wherein the cells having the expression regulatory sequence are transformants.

(7) The above screening method, wherein the test substance is a mixture.

(8) A kit for screening a substance inhibiting the activation of NF-κB, which comprises the above cells.

(9) A compound which inhibits the activation of NF-κB and which can be obtained by the above screening method.

(10) A pharmaceutical composition for the medical treatment of a disease involving extraordinary activation of NF-κB, which comprises the above compound as an active ingredient.

(11) Use of the above compound for the preparation of a pharmaceutical composition for the medical treatment of a disease caused by the activation of NF-κB.

(12) A method for the medical treatment or prevention of a disease involving extraordinary activation of NF-κB, which comprises administering the above compound.

The DNAs forming the 5'-flanking region, 5'-UTR, 3'-UTR and 3'-flanking region of the hiNOS gene includes not only DNAs isolated from humans cells but also DNAs produced by synthesis. These DNAs obtained by chemically modifying these DNAs, and the DNAs obtained by subjecting these nucleotides to alteration such as substitution, deletion and addition are also used so long as their ability to control the expression is maintained. In addition, the DNA which forms the 3'-flanking region of the hiNOS gene and which is appropriately used in the present invention is, for example, a DNA having a nucleotide sequence described in SEQ ID NO: 15 (sequence outside the frame in FIG. 5).

Any gene encoding peptide and protein can be used as the reporter gene of the present invention so long as the activity or production amount (including the production amount of mRNA) of the expression product of the gene can be measured by those skilled in the art. For example, as explained above, chloramphenicol acetyltransferase (CAT), β-galactosidase (β-Gal), luciferase, and the like can be used for measuring the enzyme activity. Moreover, secreted growth hormone, etc. can be utilized by measuring the production amount using the immunological reaction, etc.

The expression vector used for evaluating the activation of NF-κB according to the present invention can be obtained by inserting an expression regulatory sequence having a NF-κB recognition sequence, and at least part of the 3'-UTR and at least part of the 3'-flanking region of a hiNOS gene into a replicable vector. Examples of the replicable vector include pUC18 and pGEM-3z which can be replicated in *Escherichia coli*.

During screening substances which inhibits the activation of NF-κB according to the present invention, one can use the cells transformed with the vector containing the regulatory sequences of the present invention, or the naturally occurring cells having the regulatory sequences described in the present invention and capable of detecting the NF-κB activation. Mammalian cells are preferably used as such cells.

Transformation can be carried out by the conventional procedures. A host chromosome into which the vector is transiently incorporated in addition to one into which the vector is permanently incorporated is employed as the transformed cell used in the present invention. Selection of a host chromosome into which the vector is permanently incorporated can be conducted by transforming a host cell with a vector obtained by incorporating a selection marker gene into the vector to be introduced, or vector simultaneously containing the vector to be introduced and a selection marker, and culturing the transformed cell in a medium where only a cell having the selection marker can live.

The substances inhibiting the activation of NF-κB can be screened in the present invention, concretely, for example, by adding an optional amount of a test substance to the transformed cells having been cultured for a given period of time, and measuring the amount of reporters expressed by the cells after a given period of time as an enzyme activity or an amount of expressed protein. The subject substance to be screened may be natural or synthetic. Moreover, it may be a single substance or a mixture of substances. For example, a candidate single substance can be tested independently, or a mixture of several candidate substances can be tested. Moreover, a combinatorial library may also be tested. Furthermore, it is also possible to test a mixture such as extracted material from cells, which has been fractionated, repeat fractionating, and finally isolate a substance influencing the activation of NF-κB.

Furthermore, screening substances which change the activity of a specific substance influencing the activation of NF-κB, in the present invention can be carried out, specifically, for example, by adding an optional amount of candidate substances to transformed cells having been cultured for a given period of time, and determining a change in the expression amount of the reporter genes in the cells after a given period of time as a change in the enzyme activation or change in the amount of expression of protein. Screening the candidate substances are carried out in the same manner as in screening substances influencing the activation of NF-κB.

The potency of substances inhibiting the activation of NF-κB according to the present invention can be determined, under the conditions that allows the cells or living tissues capable of activation mammalian NF-κB, by adding or administering the substance, and examining the degree of lowering the production amount of NO or inflammatory protein such as TN-α released in a culture medium, blood, urea, etc. An amount of formed NO can be measured by a known method represented by the Griess method; the production amount of inflammatory protein can be determined, if preparation of the antibody is possible, by enzyme immuno assay. Moreover, the physiological activity indexed by proliferation of the cells, etc. can be determined.

Figure 11:
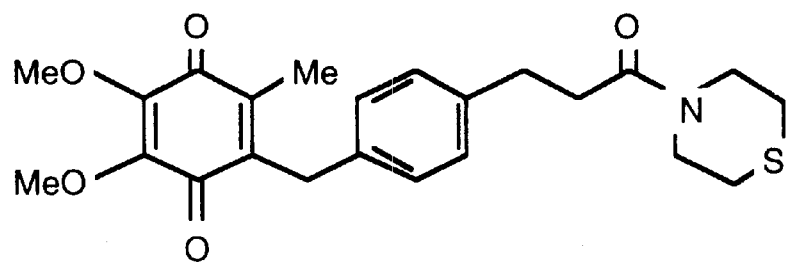
FIG. 11 shows the chemical formula of a compound I.

A compound represented by the chemical formula in FIG. 11 is mentioned as one of the examples of compounds which inhibit the activation of NF-κB and which can be obtained by the screening method or by the use of the screening kit of the present invention as explained above.

Since the substances according to the present invention can directly or indirectly inhibit the activation of NF-κB, the effects of the substances as preventives or remedies on such diseases caused by excessive activation of NF-κB such as diseases caused by the excessive production of inflammation mediators and proliferation of viruses are expected. Specifically, for example, the substances are useful as remedies and preventives against such diseases thought to be caused by the excessive production of NO and TNF-α such as septic shock, osteoarthritis, chronic rheumatoid arthritis, cachexia, inflammatory enterogenous disease, malaria, AIDS, human T cell leukemia, meningitis, hepatitis, II type diabetes, disseminated sclerosis, Behcet's syndrome, systemic lupus erythematodes and ischemic cardiopathy.

When a compound obtained by the use of the screening method or screening kit of the present invention is used as the medicinal composition mentioned above, it can be used either orally in the form of tablets, capsules, elixir, microcapsules, and the like, or parenterally in the form of injections of a solution or suspension with water or pharmaceutically allowable liquid other than water. For example, the medicinal composition can be produced by mixing the compound with physiologically allowable material such as carriers, flavors, excipients and stabilizing agents, in a generally allowed manner.

Examples of additives which can be mixed in tablets, etc. include binders such as gelatin, swelling agents such as cornstarch, excipients such as crystalline cellulose and lubricants such as magnesium stearate. When the composition is used in the form of capsules, the above composition can be made to further contain a liquid carrier. A conventional formulation can be applied to a germ free composition for injection.

Examples of the aqueous solution for injection include an isotonic solution containing glucose, etc. The aqueous solution for injection may be used in combination with suitable solution assistants such as polyethylene glycol. Moreover, buffers, stabilizing agents, preserving agents, antioxidants, agents for soothing, etc. may also be mixed. Such a formulation thus obtained can be administered to, for example, mammals including humans. Although the dose differs depending on the symptom, it is from about 0.01 to 100 mg, preferably from about 0.1 to 50 mg, more preferably from about 1.0 to 25 mg per day for an ordinary adult when orally administered. When the formulation is parenterally administered, for example, as injections, it is preferably administered by intravenous injection with a dose of from about 0.001 to 50 mg, preferably from about 0.01 to 25 mg, more preferably from about 0.1 to 10 mg per day for an ordinary adult.

EXAMPLES

The present invention will be explained more concretely with reference to examples.

Example 1

Construction of an Expression Vector

1) Cloning the 5'-Flanking Region of hiNOS

A probe for screening a clone containing the 5'-flanking region DNA of hiNOS was prepared by plaque hybridization from a human genome library (Clontech, U.S.A., a phage library incorporated into an EMBL 3 vector) consisting of $2.5 \times 10^6$.

The probe was prepared as explained below. Rat-derived iNOS cDNA (VSM-NOS) (Nunokawa, Y., Ishida, N. and Tanaka, S. (1993) Biochem. Biophys. Res. Commun., 191, 89–94) having been isolated by the present inventors was used as a template. SU802 primer (corresponding to bases −138 to −117 of rat VSM-NOS cDNA/SEQ ID NO: 3, FIG. 4) and MI103 primer (corresponding to bases 168 to 188 of rat VSM-NOS cDNA/SEQ ID NO: 4, FIG. 4) were used, and amplified cDNA was obtained by a polymerase chain reaction (PCR) and used. The PCR was performed using Taq polymerase (Takara Shuzo, K. K.) and a buffer attached thereto. It is evident that the cDNA has high homology with the nucleotide sequence at the 5'-terminal of a hiNOS structure gene. The plaque hybridization was carried out by using a ECL direct DNA labeling detection system (Amarsham, Britain), and following the experimental procedure.

The positive plaque was purified using a Qiagen lambda kit (Qiagen, Germany), and digested with EcoR I. It was confirmed that about 5 kb of DNA was hybridized by Southern blotting analysis using the probe.

About 5 kb of the DNA thus digested with EcoR I was subcloned at the EcoR I site of a pUC 118 plasmid (Takara Shuzo, K. K.). A mutant plasmid was then prepared by substituting for the nucleotide sequence as shown in FIG. 3 (SEQ ID NO: 11) for the purpose of preparing a Nco I recognition site. Using a kit of Clontech, the plasmid was prepared in accordance with the experimental procedure. The mutant plasmid was then digested with Kpn I and Nco I, and the resultant DNA fragment was used in the experiment mentioned below in 3).

2) Cloning the about 1-kb Gene Fragment of hiNOS

Containing the 3'-UTR and Its Downstream

The human genome library used in 1) mentioned above was divided into 60 subpools (about 40,000 clones per pool). Two types of forward primers (SA101/SEQ ID NO: 5, SA102/SEQ ID NO: 7) and two types of reverse primers (KI101/SEQ ID NO: 6, KI102/SEQ ID NO: 8) were prepared (FIG. 4) based on the sequence (within the frame in FIG. 5) of the 3'-UTR of cDNA in hiNOS, and the pool containing the 3'-UTR was identified by a PCR. The positive pool was divided into 30 subpools, and a pool containing the positive clones was identified by a similar PCR.

At this moment, the pool was thought to contain at least about 1,000 clones based on calculation. A phage containing the entire clones of the identified subpool was cultured. The phage DNA was purified using a Qiagen lambda kit (Qiagen), and amplification of DNA was observed by a PCR using SA101 and KI101. Accordingly, it was confirmed that the 3'-UTR of hiNOS was contained. The occurrence of the PCR was confirmed in the same manner as in 1) mentioned above.

Next, the DNA of the downstream portion containing the 3'-UTR was amplified by a PCR using the forward primer (SA101) and a reverse primer (KI103/SEQ ID NO: 9, FIG. 4) having been prepared on the basis of the nucleotide sequence of the SP6 promoter portion on the EMBL 3 right arm on the phage vector while the purified DNA was used as a template. The amplified DNA sequence was determined by direct sequencing with a fluorescent sequencer. The results are shown in the SEQ ID NO: 13 and FIG. 5.

Since it could be confirmed by nucleotide sequence analysis that the amplified DNA was a region containing the 3'-UTR of hiNOS, the poly(A) addition site was determined based on the information, and the KI105 reverse primer (SEQ ID NO: 12) was prepared on the basis of the nucleotide sequence of the 3'-flanking region (FIG. 4, FIG. 5).

About 1 kb of DNA containing the 3'-UTR and 3'-flanking region was amplified by a PCR using SA103 (SEQ ID NO: 10, FIG. 4) and KI105 while the purified DNA was employed as a template. Since SA103 had an Nhe I recognition site introduced at the 5'-terminal and KI105 had a BamH I recognition site introduced at the 5'-terminal, the DNA was digested with BamH and Nhe I, and the resultant DNA fragment (3'-UTR+3'-flanking region) was used in the experiment in 3) described below.

3) Construction of Each Plasmid Which is pGL3/hiNOS (FIG. 6)

A. Construction of the Plasmid pGLNOS5+SV3

In order to construct PGLNOS5+SV3 in which the 5'-flanking region and 5'-UTR were inserted into the upstream of the luciferase gene of a pGL3 basic plasmid, the pGL3 basic plasmid (Promega, U.S.A.) was digested with the restriction enzymes Kpn I and Nco I, and the DNA fragment having been prepared in 1) was inserted into the digested portion (FIG. 6A).

B. Construction of the Plasmid pGLNOS3A

In order to construct the plasmid PGLNOS3A wherein the region from directly below the termination codon to the signal region containing added SV40-derived poly(A) of the luciferase gene contained in a pGL3 basic plasmid was removed, and an about 1-kb fragment alone containing the 3'-UTR and 3'-flanking region of a hiNOS gene was inserted into the downstream of the pGL3 basic luciferase gene in place of the removed portion, a pGL3 basic plasmid was digested with BamH I and Xba I, and the DNA fragment (3'-UTR+3'-flanking region) having been prepared in 2) was inserted into the digested region (FIG. 6B).

C. Construction of the Plasmid pGLNOS53A

In order to construct the plasmid pGLNOS53A wherein the 5'-flanking region and 5'-UTR of a hiNOS gene were inserted into the upstream of a pGL3 basic luciferase gene, the region from directly below the termination codon to the signal region containing added SV 40-derived poly(A) of the luciferase gene was removed, and about 1 kb of a fragment containing the 3'-UTR and 3'-flanking region of a hiNOS gene was inserted in place of the removed portion, a pGL3 basic plasmid was digested with BamHI and XbaI, and the DNA fragment (3'-UTR+3'-flanking region) having been prepared in 2) was inserted into the digested portion. The plasmid thus obtained was digested with the restriction enzymes Kpn I and Nar I, and the DNA fragment having been prepared in 1) was inserted into the digested portion (FIG. 6C).

Example 2

Reaction in the Transient Expression System of pGL3/hiNOS

Human lung cancer-derived cells A549 known to express hiNOS by cytokine stimulation was obtained from ATCC (catalogue No.: CCL185), and cultured in a GIT medium (Wako Junyaku, K. K.) in an incubator (5% $CO_2$). Each pGL3/hiNOS plasmid having been prepared in Example 1 was transiently introduced into the A549 cells, and human IL-1 β (1 ng/ml) and human IL-1 β (1 ng/ml)+human IFN-γ (1,000 U/ml)+human TNF-α (500 ng/ml) (sometimes the mixture being termed CM hereinafter) were added, followed by examining the reaction after 6 hours (FIG. 7).

The activity of the luciferase was measured in accordance with the protocol of the luciferase assay system (Promega, U.S.A.). Human IL-1 β was purchased from Genzyme (U.S.A.). Human IFN-γ and human TNF-α having been produced by conventional procedures at Suntory Biomedical Research Institute were used. In the experiment, in order to standardize the assay, β-Gal expression vectors (pSV-β-Gal control vectors, Promega) were introduced as control vectors at the same time to correct the results.

When pGLNOS5+SV3 was introduced, high expression at the time of nonstimulation was observed, and strong induction by the cytokine was not observed. When a pGLNOS3A plasmid deficient in the 5'-flanking region was employed, neither the expression at the time of nonstimulation nor the induction of the expression caused by stimulation with the cytokine was observed.

However, when pGLNOS53A which is a plasmid containing the 3'-UTR and 3'-flanking region of a hiNOS gene was used, expression of the luciferase at the time of non-stimulation was not observed substantially; high expression came to be observed only after addition of IL-1β; very high expression came to be observed when three types of cytokine were added. That is, it has been found that expression regulation of a hiNOS gene is carried out by the upstream portion containing the 5'-UTR and the downstream portion containing the 3'-UTR in corporation. consequently, it has been shown that the plasmid used in the present invention can be realized only by inserting at least a portion of the 5'-UTR and at least a portion of the 3'-UTR into both the front and the rear of the reporter gene; the plasmid of the invention cannot be realized by inserting only one of the two regions.

Example 3

Preparation of the Transformants (A549/hiNOSLuc and A549/NF-κBLuc)

In order to prepare an A549 cell (A549/hiNOSLuc) containing stably introduced pGLNOS53A and an A549 cell (A549/NF-κBLuc) containing a stably introduced luciferase plasmid (pNF κB-Luc) which was regulated by a NF-κB recognition sequence, the following procedure was conducted. That is, using Lipofectamine (Lifetech Oriental, Tokyo), pGLNOS53A or pNF κB-Luc (Stratagene, U.S.A.) and pSV2neo (Clontech, U.S.A.) were simultaneously transfected into the A549 cell, and G418 sulfate (1 mg/ml, Lifetech Oriental) was added to the culture medium to select a cell (A549/hiNOSLuc and A549/NF-κBluc) containing stably introduced pGLNOS53A or pNF κB-Luc.

Example 4

Reaction of A549/hiNOSLuc and A549/NF-κBLuc against Cytokine Stimulation

As shown in Table 1, the reaction against cytokine was investigated. A549/hiNOSLuc reacted even when IL-1β alone was added. However, addition of the three types of cytokine IL-1β+IFN-γ+TNF-α (CM), which is essential to the induction of hiNOS, significantly increased the induction by a factor of at least 500 as compared with the induction of a control.

On the other hand, when A549/NF-κBLuc was employed, it showed a reaction different from the case of expression induction of hiNOS: induction was caused by the stimulation of IL-1β or TNF-α alone; the influence of the action of IFN-γ in corporation was insignificant, and the induction increased by a maximum factor of about 40. The following can be concluded from what is explained above: the signal activating pGLNOS53A is differentiated from that activating pNF-κBluc; and A549/hiNOSLuc is useful for evaluating the activation of NF-κB participating in the expression of hiNOS.

TABLE 1

| Cytokine used for stimulation | Induction Factor of Luciferase | |
|---|---|---|
| | A549/hiNOSLuc | A549/NF-KBluc |
| Control | 1 | 1 |
| IL-1β | 8.6 | 32.2 |
| IL-1β + IFN-γ | 46 | 36.8 |
| TNF-α | 7.6 | 40.4 |
| IL-1β + IFN-γ + TNF-α | 555 | 42.2 |

Example 5

Gene Sequence Participating in Expression Induction of hiNOS

It is possible to observe the binding proteins by cytokine stimulation to the double strand DNA which corresponds to the nucleotides −131 to −97 upstream of the transcriptional start site of the hiNOS gene and which contains the NF-κB recognition sequence (Nos. 17 (G) to 26 (C) in SEQ ID NO: 14) by gel shift assay.

The gel shift assay was carried out by making the digoxigenin (DIG)-labelled DNA, incubating the resultant sequence and a nuclear fraction extracted from A549 cells, and subjecting the incubated portion to electrophoresis at 4° C. using 7.5% polyacrylamide gel. Moreover, the nuclear fraction of the cells had been extracted by the following procedure: the cells were either not stimulated, or stimulated with IL-1β (1 ng/ml) or CM for 4 hours; and the nuclear fraction was extracted by the Schreiber's method (Schreiber, E., Matthias, P., Muller, M. M., and Schaffner, W. (1989) Nucleic Acids Res. 17, 6419). The DNA having been subjected to electrophoresis in the gel was transferred to a nylon film using electrotransfering, and the DNA labeled with DIG was detected with a DIG recognition antibody showing chemiluminescence. DIG-labelling and detection were carried out by using Gel Shift Assay Kit (Boehringer Mannheim, Germany).

Figure 8:
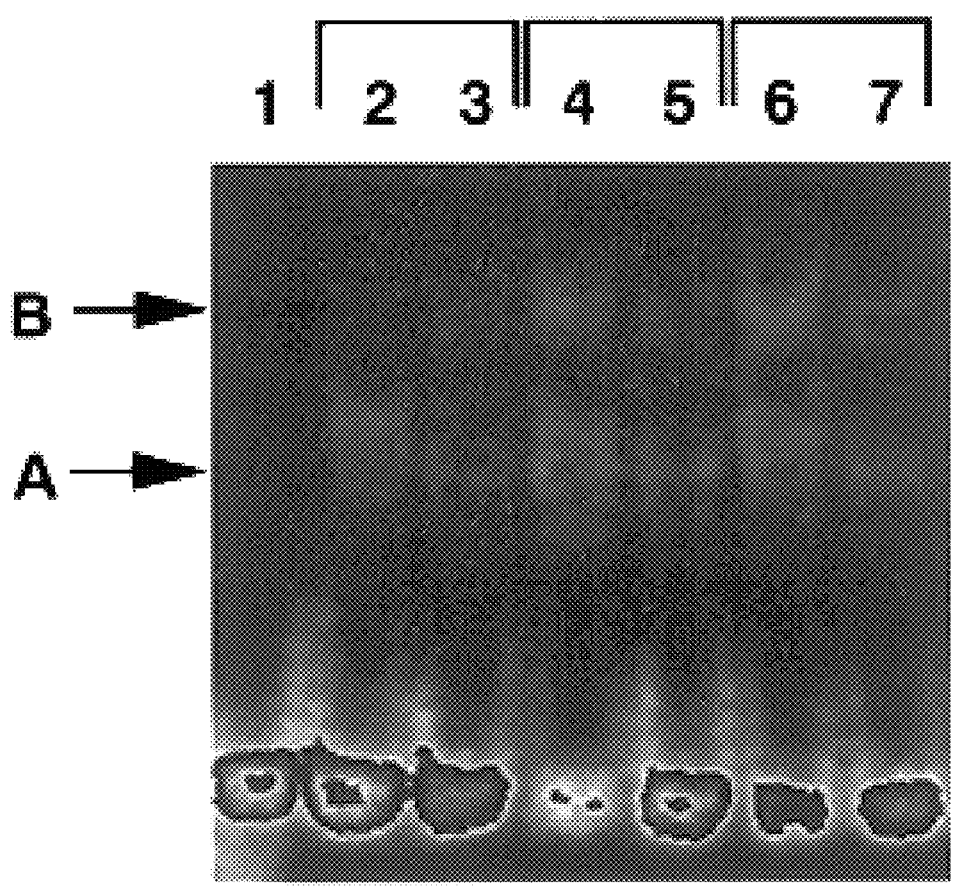
FIG. 8 shows the results of gel shift assay of a nuclear extraction substance at the time of cytokine stimulation of an A549 cell. There is no extracted substance in lane 1; there is no cytokine stimulation in lanes 2 and 3; there is stimulation with IL-1β for 4 hours in lanes 4 and 5; there is stimulation with CM for 4 hours in lanes 6 and 7. A DIG-free probe having a concentration 20 times as much is added in lanes 3, 5 and 7.

FIG. 8 shows the results. The following have been found from the results: protein (corresponding to band A of FIG. 8), which exists in the A549 nuclear extract in the absence of stimulation, binds to the above sequence; however, other protein (corresponding to band B of FIG. 8) comes to strongly binds thereto by stimulation with IL-1β and CM.

It can be concluded from what is explained above that the NF-κB recognition sequence responsive to cytokine stimulation is included in the 5'-flanking region of the hiNOS gene used in the present invention.

Example 6

Confirmation with Known Compounds

It has been confirmed that the screening method according to the present invention can evaluate the activation of NF-κB with compounds known to inhibit the activation of NF-κB.

1) Evaluation with Glucocorticoid

Dexamethasone (Dex) has powerful anti-inflammation action, and one of the action mechanisms is known to be the inhibition of activation of the transcription factor NF-κB (Ray, A., and Prefontaine, K. E. (1994) Proc. Natl. Acad. Sci. USA, 91, 752–755).

Figure 9:
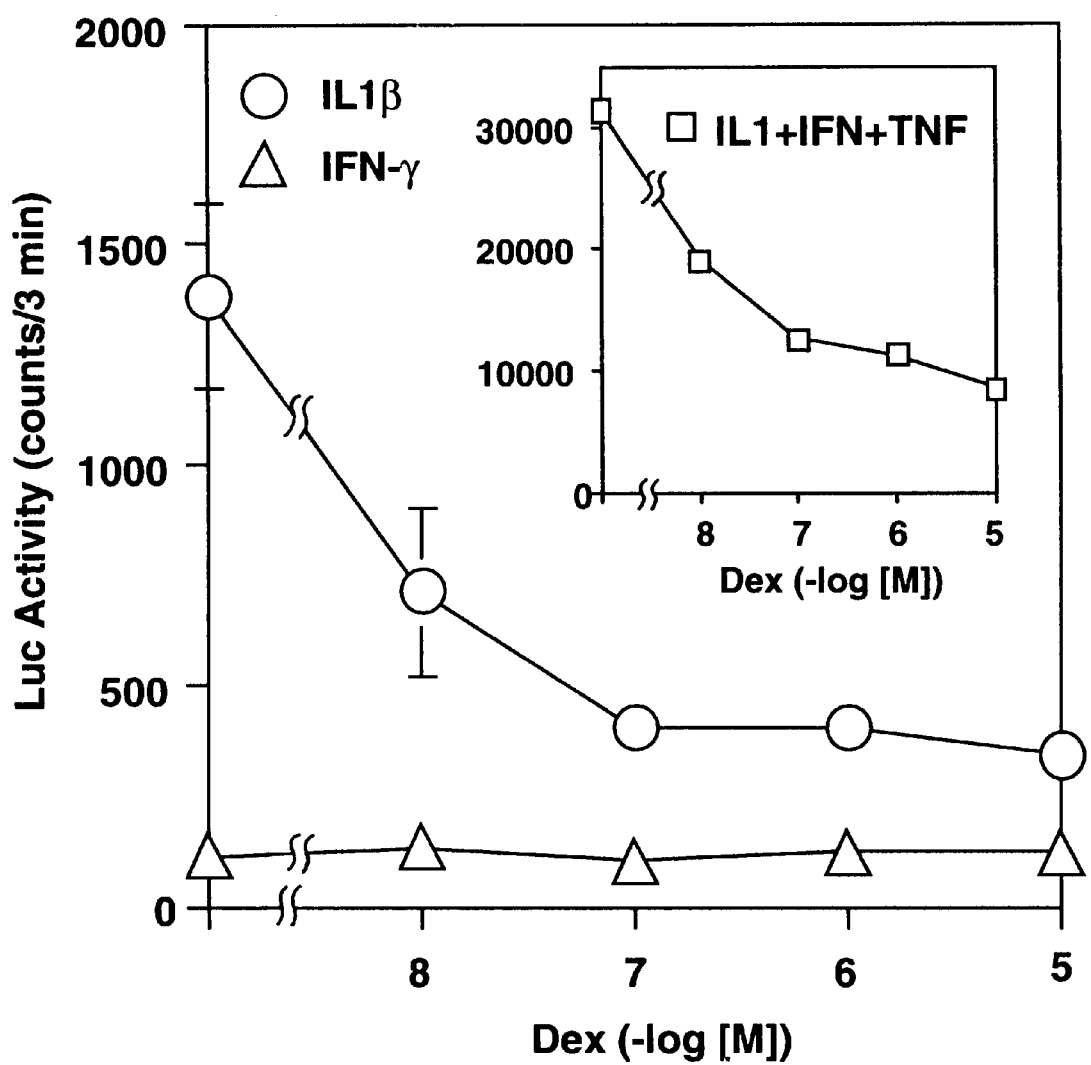
FIG. 9 is a graph showing the influence of dexamethasone in the presence of cytokine.

Dex of a concentration of up to 10 μM inhibited the expression of a reporter gene which was to be activated when treated with IL-1β (1 ng/ml) and CM for 24 hours (FIG. 9).

2) Influence of Protease Inhibitors

Proteases are thought to participate in the activation of NF-κB through the decomposition of I-kB (protein inhibiting the activation of NF-κB within cytoplasm). TLCK which is one of the proteolytic enzyme inhibitors is known to inhibit the activation of NF-κB (Griscavage, J. M., Wilk, S., and Ignarro, L. J. (1995) Biochem. Biophys. Res. Commun., 215, 721–729).

Figure 10:
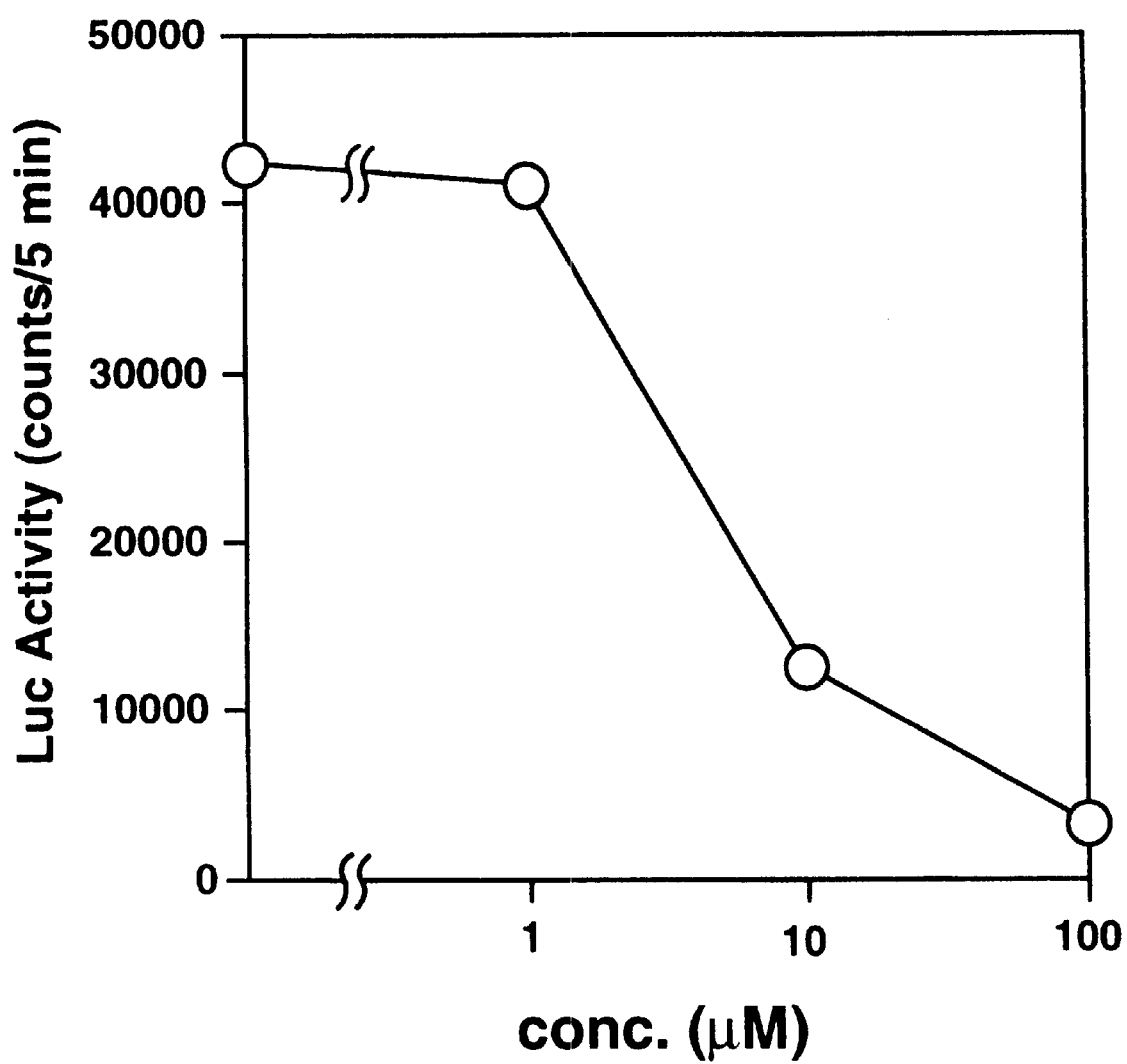
FIG. 10 is a graph showing the effects of a protease inhibitor (TLCK) on hiNOS induction caused by CM stimulation.

As a result of carrying out an experiment similar to that in 1), TLCK showed that it inhibited the expression caused by IL-1β (1 ng/ml) and CM at the concentration of about 10 μM (FIG. 10).

It has been demonstrated from the experimental results as mentioned above that compounds known to inhibit the activation of NF-κB can be evaluated by the screening method according to the present invention.

Example 7

Compounds Influencing the Activation of NF-κB

Figure 12:
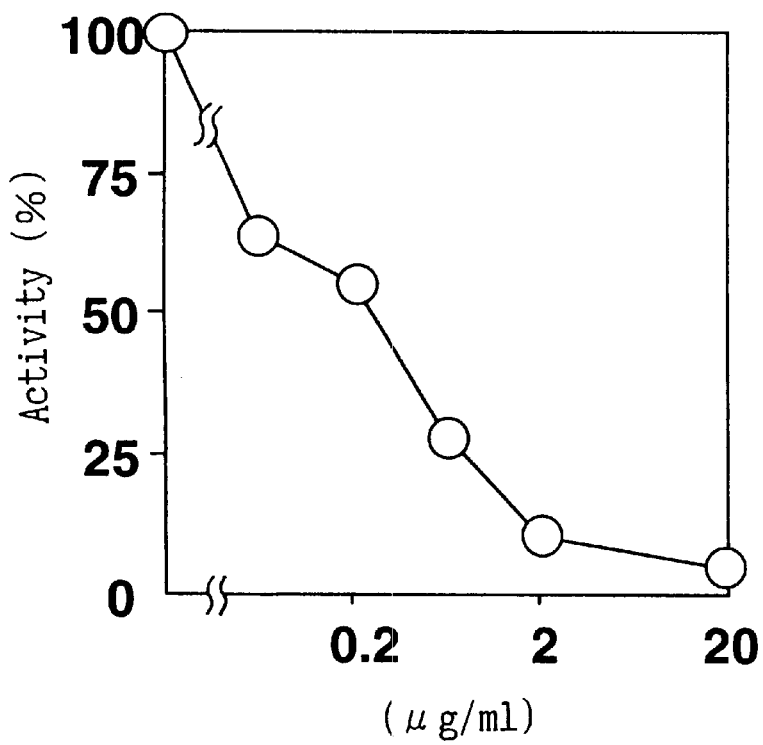
FIG. 12 is a graph showing the influence of the compound I in the assay system according to the present invention.
Figure 13:
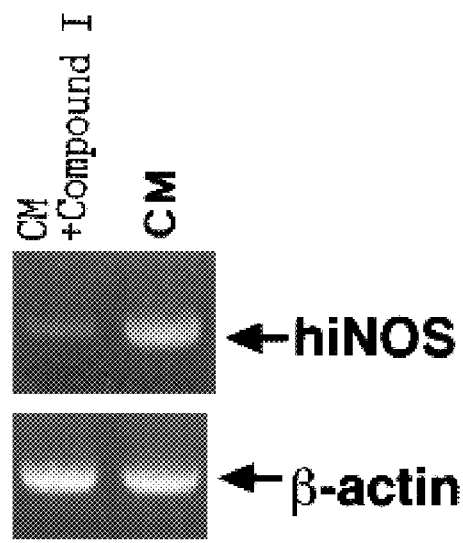
FIG. 13 shows the influence of the compound I on the mRNA expression of hiNOS by using reverse transcriptase-PCR method.

A compound or a mixture of compounds which was unknown to influence the activation of NF-κB was added to A549 cells 1 hour before adding IL-1β and TNF-α, and the luciferase activity was measured 24 hours thereafter by the same procedure as in Example 6. As a result, it has become clear that the compound I which is a phenylmethylbenzoquinone derivative (FIG. 11) represses the luciferase activity with the repression depending on the concentration of the compound I (FIG. 12). Moreover, it clear that the compound I also represses the expression of hiNOS mRNA caused by CM stimulation (FIG. 13).

Example 8

Action of the Compound I (1)

Figure 14:
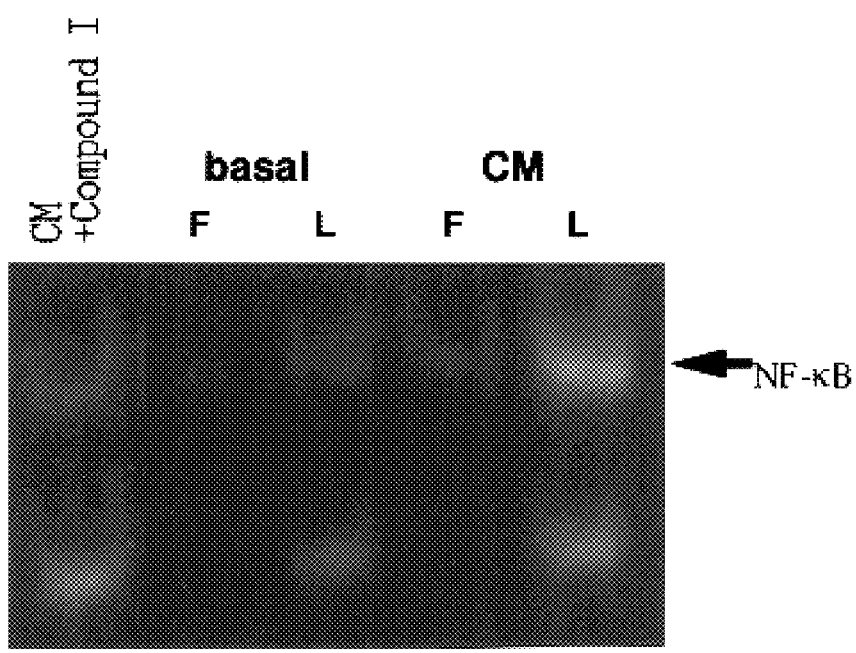
FIG. 14 shows that the compound I inhibits the activation of NF-κB after CM stimulation, the results being confirmed by gel shift assay.

When the gel shift assay was practiced in accordance with the method explained in Example 5, it was confirmed that the compound I (20 μg/ml) having been found by the present screening method inhibited the activation of the NF-κB of A549 cells to which cytokine had been added (FIG. 14).

Furthermore, it was confirmed that when A549/NF-κBLuc was stimulated with IL-1β or TNF-α, the compound I inhibited the luciferase activity (FIG. 15).

Example 9

Action of the Compound I (2)

The Griess method utilizing a diazo reaction has been known as a method for indirectly knowing that a cell actually produces NO (Green, L. C., Wagner, D. A., Glogowski, J., Skipper, P. L., Wishnok, J. S., and Tannenbaum, S. R. (1982) Anal. Biochem., 126, 131–138). In the Griess method, the Griess reagent which is a mixture of naphthylethylenediamine and sulfanilic acid is reacted with an $NO_2$ ion in a culture medium, and the color development is determined by absorption at 540 nm. As a result of measuring the amount of NO accumulated in a cell culture medium after 24 hours by the method, it became evident that the compound I inhibited the production of NO released from RAW 264.7 cells (ATCC catalogue No.: TIB-71) having been stimulated with lipopolysaccharide (LPS) (FIG. 16A).

Example 10

Action of the compound I (3)

Although it has been known that TNF-α is produced when NF-κB is activated by LPS stimulation (Blackwell, T. S. and Christman, J. W. (1997) Am. J. Respir. Cell. Mol. Biol., 17, 3–9, Collins, T., Read, M. A., Neish, A. S., Whitley, M. Z., Thanos, D. and Maniatis, T. (1995) Faseb. J., 9, 899–909), it is astonishing to find that the compound I inhibits the production of TNF-α inhibits from RAW264.7 cells having been stimulated with LPS for 4 hours (FIG. 16B).

Furthermore, mRNA extracted from the RAW264.7 cells was detected by the reverse transcriptase PCR method, and the inhibition mechanism was found to be inhibition at the gene expression level of iNOS and TNF-α (FIG. 17).

The results as explained above show that the screening method according to the present invention is also useful for finding a substance which has been unknown to be useful for repressing the activation of NF-κB.

The present inventors have discovered that a compound having the action of inhibiting the activation of NF-κB can be evaluated simply and highly sensitively by preparing a plasmid maintaining the function of the 5'-promoter region and 3'-untranslated region of a hiNOS gene, and using a human cells into which the plasmid has been stably introduced.

Furthermore, it has been discovered by the method according to the present invention that phenylmethylbenzoquinone derivatives which have been known as remedies for improving brain functions have a function of inhibiting NF-κB.

Examples in the specification of the present invention have shown that the method of the present invention is useful for the purpose of screening a compound repressing the activation of NF-κB and a compound repressing the excessive expression of protein induced by the activation of NF-κB, simply and highly sensitively.

A compound repressing the activation of NF-κB is expected to be effective as a preventive and a remedy against diseases caused by excessive production of various inflammation mediators and proliferation of a virus.

The method according to the present invention is useful for searching for the medical treatment and preventives against such diseases thought to be caused by the excessive production of NO and TNF-α as septic shock, osteoarthritis, chronic rheumatoid arthritis, cachexia, inflammatory enterogenous disease, malaria, AIDS, human T cell leukemia, meningitis, hepatitis, II type diabetes, disseminated sclerosis, Behcet's syndrome, systemic lupus erythematodes and ischemic cardiopathy.

What is claimed is:

1. An isolated expression regulatory sequence comprising an NF-KB recognition sequence, and a 3'-untranslated region (3'-UTR) and a 3'-flanking region of a human inducible nitrogen monoxide synthase (hiNOS) gene, wherein said 3'-UTR and said 3'-flanking region confer inducible expression on an upstream coding sequence.

2. An isolated expression regulatory sequence according to claim 1, wherein the 3'-flanking region of a hiNOS gene comprises the nucleotide sequence of SEQ ID NO: 15.

3. An isolated expression vector comprising an expression regulatory sequence according to claim 1.

4. An isolated expression vector according to claim 3, wherein the expression vector further comprises a reporter gene.

5. An isolated expression vector comprising, in the following order going from 5' to 3': (1) the 5'-flanking region containing the promoter region of a hiNOS gene, (2) a reporter gene and (3) the expression regulatory sequence according to claim 1.

6. An isolated cell transformed with an expression vector according to claim 3.

7. A method of screening for a substance which represses activation of NF-KB, which comprises treating cells having an expression regulatory sequence according to claim 1 which is operably linked to a reporter gene, with a test substance, and observing any changes in the expression level of the reporter gene, wherein a decrease in the expression level indicates that the test substance is a substance which represses activation of NF-KB.

8. A screening method according to claim 7, wherein the test substance is a composition of two or more substances.

9. An isolated expression vector comprising an expression regulatory sequence according to claim 2.

10. An isolated expression vector comprising, in the following order going from 5' to 3': (1) the 5'-flanking region containing the promoter region of the hiNOS gene, (2) a reporter gene and (3) the expression regulatory sequence according to claim 2.

11. An isolated cell transformed with an expression vector according to claim 5.

12. A method of screening for a substance which represses activation of NF-KB, which comprises treating cells having an expression regulatory sequence according to claim 2 which is operably linked to a reporter gene, with a test substance, and observing any changes in the expression level of the reporter gene, wherein a decrease in the expression level indicates that the test substance is a substance which represses activation of NF-KB.

13. An isolated expression regulatory sequence according to claim 1, wherein the 3'-UTR comprises the nucleotide sequence of SEQ ID NO: 2.

14. An isolated expression regulatory sequence according to claim 2, wherein the 3'-UTR comprises the nucleotide sequence of SEQ ID NO: 2.

15. A method according to claim 7, wherein the 3'-UTR comprises the nucleotide sequence of SEQ ID NO:2.

16. A method according to claim 7, wherein the 3'-flanking region comprises the nucleotide sequence of SEQ ID NO:15.

17. A screening method according to claim 16, wherein the 3'-UTR comprises the nucleotide sequence of SEQ ID NO: 2.

* * * * *

SEQUENCE LISTING

<160> NUMBER OF SEQ ID NOS: 15

<210> SEQ ID NO 1
<211> LENGTH: 296
<212> TYPE: DNA
<213> ORGANISM: SV40
<220> FEATURE:
<223> OTHER INFORMATION: Genomic DNA for SV40

<400> SEQUENCE: 1
ctagagtcgg ggcggccggc cgcttcgagc agacatgata agatacattg atgagtttgg    60
acaaaccaca actagaatgc agtgaaaaaa atgctttatt tgtgaaattt gtgatgctat   120
tgctttattt gtaaccatta taagctgcaa taaacaagtt aacaacaaca attgcattca   180
ttttatgttt caggttcagg gggaggtgtg ggaggttttt taaagcaagt aaaacctcta   240
caaatgtggt aaaatcgata aggatccgtc gaccgatgcc cttgagagcc ttcaac       296

<210> SEQ ID NO 2
<211> LENGTH: 604
<212> TYPE: DNA
<213> ORGANISM: Homo sapiens
<220> FEATURE:
<223> OTHER INFORMATION: Genomic DNA coding for hiNOS

<400> SEQUENCE: 2
agccagaagc gctatcacga agatatcttc ggtgctgtat ttccttacga ggcgaagaag    60
gacagggtgg cggtgcagcc cagcagcctg gagatgtcag cgctctgagg gcctacagga   120
ggggttaaag ctgccggcac agaacttaag gatggagcca gctctgcatt atctgaggtc   180
acagggcctg gggagatgga ggaaagtgat atcccccagc ctcaagtctt atttcctcaa   240
cgttgctccc catcaagccc tttacttgac ctcctaacaa gtagcaccct ggattgatcg   300
gagcctcctc tctcaaactg gggcctccct ggtcccttgg agacaaaatc ttaaatgcca   360
ggcctggcga gtgggtgaaa gatggaactt gctgctgagt gcaccacttc aagtgaccac   420
caggaggtgc tatcgcacca ctgtgtattt aactgccttg tgtacagtta tttatgcctc   480
tgtatttaaa aaactaacac ccagtctgtt ccccatggcc acttgggtct tccctgtatg   540
attccttgat ggagatattt acatgaattg cattttactt taatcacaaa aaaaaaaaaa   600
aaaa                                                                604

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 3
cttctcagcc accttggtga gg                                             22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:Primer

<400> SEQUENCE: 4
ttctgtgcag tcccagtgag g                                              21

```
<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:Primer

<400> SEQUENCE: 5
agccagaagc gctatcacg                                            19

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 6
tgtgattaaa gtaaaatgca attcatg                                   27

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 7
gcctggagat gtcagcgctc tg                                        22

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:Primer

<400> SEQUENCE: 8
ggggaacaga ctgggtgtta g                                         21

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:Primer

<400> SEQUENCE: 9
catttaggtg acactatag                                            19

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 10
ggcgctagcc tacaggaggg gttaaagct                                 29

<210> SEQ ID NO 11
<211> LENGTH: 27
<212> TYPE: DNA
<213> ORGANISM: Artificial Sequence
<220> FEATURE:
```

```
<223> OTHER INFORMATION: Description of Artificial Sequence:Primer

<400> SEQUENCE: 11
atggcctgtc ccatggaaat ttctgtt                                              27

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 12
gcgcggatcc ggcccactct cctaag                                               26

<210> SEQ ID NO 13
<211> LENGTH: 1026
<212> TYPE: DNA
<213> ORGANISM: Homo sapiens
<220> FEATURE:
<223> OTHER INFORMATION: Genomic DNA for hiNOS

<400> SEQUENCE: 13
tgagggccta caggaggggt taaagctgcc ggcacagaac ttaaggatgg agccagctct          60
gcattatctg aggtcacagg gcctggggag atggaggaaa gtgatatccc ccagcctcaa         120
gtcttatttc ctcaacgttg ctccccatca agccctttac ttgacctcct aacaagtagc        180
accctggatt gatcggagcc tcctctctca aactggggcc tccctggtcc cttggagaca        240
aaatcttaaa tgccaggcct ggcgagtggg tgaaagatgg aacttgctgc tgagtgcacc       300
acttcaagtg accaccagga ggtgctatcg caccactgtg tatttaactg ccttgtgtac       360
agttatttat gcctctgtat ttaaaaaact aacacccagt ctgttcccca tggccacttg      420
ggtcttccct gtatgattcc ttgatggaga tatttacatg aattgcattt tactttaatc    480
acactgtatg cgtgtgtggg tgttttgtag ggaaagctct tctcagagtg gggagctggt   540
gggtgtcaca gcctggacag atccccgaca gagggacacc ccagccagtc catggctcct  600
ctgaaatggc tgccaggtgt gccagcagca gatggagctt cgtgctggtc caaagacctg  660
tggtagggca gggggcgcag gcctgcctcc cacacaaagt atctgaaacg gggtctggtg  720
agggtgggat tgtcgcataa ggccagtgtt tcgaggaagg ccttgagctt cttcttggac  780
actgtcttag aaagcgtttt gctctggggc caccagtctc atgcgagact gtgtgccttg  840
gccagtacgg atgtggtccc tgggaaggca gcgtgtcgag gcgagtgtgg gccacaacat  900
cctcgcctga gggactgggg accctcttgg gtttggagca ggccaaggaa tccttcttag  960
gagagtgggc cccgtttcct tctcctggtc agaacccaaa aaggagctca gcggcggcca 1020
ctgggg                                                              1026

<210> SEQ ID NO 14
<211> LENGTH: 35
<212> TYPE: DNA
<213> ORGANISM: Homo sapiens
<220> FEATURE:
<223> OTHER INFORMATION: Synthetic DNA based on genomic DNA for hiNOS

<400> SEQUENCE: 14
aactgtacac aagctgggga cactcccttt ggaaa                                     35

<210> SEQ ID NO 15
<211> LENGTH: 544
```

```
<212> TYPE: DNA
<213> ORGANISM: Homo sapiens
<220> FEATURE:
<223> OTHER INFORMATION: 3'-flanking region of genomic DNA for hiNOS

<400> SEQUENCE: 15
actgtatgcg tgtgtgggtg ttttgtaggg aaagctcttc tcagagtggg gagctggtgg      60
gtgtcacagc ctggacagat ccccgacaga gggacacccc agccagtcca tggctcctct     120
gaaatggctg ccaggtgtgc cagcagcaga tggagcttcg tgctggtcca aagacctgtg     180
gtagggcagg gggcgcaggc ctgcctccca cacaaagtat ctgaaacggg gtctggtgag     240
ggtgggattg tcgcataagg ccagtgtttc gaggaaggcc ttgagcttct tcttggacac     300
tgtcttagaa agcgttttgc tctggggcca ccagtctcat gcgagactgt gtgccttggc     360
tagtacggat gtggtccctg ggaaggcagc gtgtcgaggc gagtgtgggc cacaacatcc     420
tcgcctgagg gactggggac cctcttgggt ttggagcagg ccaaggaatc cttcttagga     480
gagtgggccc cgtttccttc tcctggtcag aacccaaaaa ggagctcagc ggcggccact     540
gggg                                                                  544
```